(12) United States Patent
Cook et al.

(10) Patent No.: US 8,920,499 B2
(45) Date of Patent: Dec. 30, 2014

(54) METHOD OF USE OF TROCHLEAR IMPLANTS

(71) Applicants: Stephen D. Cook, New Orleans, LA (US); Peter Strzepa, Austin, TX (US); Shoib Bajaj, Kenner, LA (US)

(72) Inventors: Stephen D. Cook, New Orleans, LA (US); Peter Strzepa, Austin, TX (US); Shoib Bajaj, Kenner, LA (US)

(73) Assignee: Fellowship of Orthopaedic Researchers, Inc., Metairie, LA (US)

( * ) Notice: Subject to any disclaimer, the term of this patent is extended or adjusted under 35 U.S.C. 154(b) by 0 days.

(21) Appl. No.: 13/855,513

(22) Filed: Apr. 2, 2013

(65) Prior Publication Data
US 2013/0226298 A1    Aug. 29, 2013

Related U.S. Application Data

(62) Division of application No. 12/868,112, filed on Aug. 25, 2010.

(60) Provisional application No. 61/236,811, filed on Aug. 25, 2009.

(51) Int. Cl.
*A61F 2/08* (2006.01)
*A61F 2/30* (2006.01)
*A61F 2/38* (2006.01)

(52) U.S. Cl.
CPC ........... *A61F 2/30756* (2013.01); *A61F 2/3877* (2013.01); *A61F 2310/00574* (2013.01); *A61F 2310/00173* (2013.01)
USPC ...................................... 623/14.12

(58) Field of Classification Search
CPC ................. A61F 2/30756; A61F 2/30; A61F 2002/30112; A61F 2002/30761; A61F 2002/30764; A61F 2002/30766
USPC ............................................ 623/14.12, 20.14
See application file for complete search history.

(56) References Cited

U.S. PATENT DOCUMENTS

| 4,158,894 A | 6/1979 | Worrell |
| 4,231,121 A | 11/1980 | Lewis |

(Continued)

FOREIGN PATENT DOCUMENTS

| CA | 2232068 | 3/1997 |
| DE | 69732500 T | 4/2006 |

(Continued)

OTHER PUBLICATIONS

Non-Final Office Action issued against U.S. Appl. No. 12/074,770 on Nov. 24, 2010; p. 1-14.

(Continued)

*Primary Examiner* — David Isabella
*Assistant Examiner* — Ann Schillinger
(74) *Attorney, Agent, or Firm* — Frommer Lawrence & Haug LLP

(57) ABSTRACT

Methods of using implant devices are provided herein. The implant devices of the methods herein have an articular end and a stem, the stem having an oval-shaped cross-section. The articular end has an upper surface, a side surface, and a lower surface. The upper surface and lower surface each intersect the side surface. The upper surface has a first surface curvature, a central surface curvature, and a second surface curvature. The stem extends from the lower surface in a direction away from the upper surface of the articular end.

20 Claims, 3 Drawing Sheets

(56) References Cited

U.S. PATENT DOCUMENTS

| | | | |
|---|---|---|---|
| 4,281,419 A | 8/1981 | Treace | |
| 4,488,843 A | 12/1984 | Achille | |
| 4,849,692 A | 7/1989 | Blood | |
| 4,919,667 A | 4/1990 | Richmond | |
| 4,945,305 A | 7/1990 | Blood | |
| 4,964,867 A | 10/1990 | Boger | |
| 5,019,104 A | 5/1991 | Whiteside et al. | |
| 5,236,462 A | 8/1993 | Mikhail | |
| 5,246,460 A | 9/1993 | Goodfellow et al. | |
| 5,263,987 A | 11/1993 | Shah | |
| 5,306,311 A | 4/1994 | Stone | |
| 5,358,525 A | 10/1994 | Fox | |
| 5,383,937 A | 1/1995 | Mikhail | |
| 5,580,353 A | 12/1996 | Mendes et al. | |
| 5,600,330 A | 2/1997 | Blood | |
| 5,609,640 A | 3/1997 | Johnson | |
| 5,645,605 A | 7/1997 | Klawitter | |
| 5,742,394 A | 4/1998 | Hansen | |
| 5,744,953 A | 4/1998 | Hansen | |
| 5,749,874 A | 5/1998 | Schwartz | |
| 5,767,669 A | 6/1998 | Hansen et al. | |
| 5,767,960 A | 6/1998 | Orman et al. | |
| 5,782,835 A | 7/1998 | Hart | |
| 5,782,927 A | 7/1998 | Klawitter et al. | |
| 5,831,260 A | 11/1998 | Hansen | |
| 5,953,683 A | 9/1999 | Hansen et al. | |
| 6,159,247 A | 12/2000 | Klawitter et al. | |
| 6,172,499 B1 | 1/2001 | Ashe | |
| 6,217,616 B1* | 4/2001 | Ogilvie | 623/20.11 |
| 6,246,231 B1 | 6/2001 | Ashe | |
| 6,417,839 B1 | 7/2002 | Odell | |
| 6,436,146 B1 | 8/2002 | Hassler et al. | |
| 6,473,167 B1 | 10/2002 | Odell | |
| 6,528,991 B2 | 3/2003 | Ashe | |
| 6,575,986 B2 | 6/2003 | Overaker | |
| 6,610,067 B2 | 8/2003 | Tallarida et al. | |
| 6,626,945 B2 | 9/2003 | Simon | |
| 6,626,950 B2 | 9/2003 | Brown | |
| 6,679,917 B2 | 1/2004 | Ek | |
| 6,699,292 B2 | 3/2004 | Ogilvie et al. | |
| 6,709,460 B2 | 3/2004 | Merchant | |
| D490,900 S | 6/2004 | Ogilvie et al. | |
| 6,754,596 B2 | 6/2004 | Ashe | |
| 6,784,660 B2 | 8/2004 | Ashe | |
| 6,797,006 B2 | 9/2004 | Hodorek | |
| 6,814,757 B2 | 11/2004 | Kopylov et al. | |
| 6,815,651 B2 | 11/2004 | Odell | |
| 6,854,972 B1 | 2/2005 | Elian | |
| 6,856,823 B2 | 2/2005 | Ashe | |
| 7,027,634 B2 | 4/2006 | Odell | |
| 7,106,431 B2 | 9/2006 | Odell | |
| 7,161,686 B2 | 1/2007 | Duling et al. | |
| 7,204,854 B2 | 4/2007 | Guederian et al. | |
| 7,264,634 B2 | 9/2007 | Schmieding | |
| 7,314,488 B2 | 1/2008 | Reiley | |
| 7,488,348 B2* | 2/2009 | Truncale et al. | 623/23.63 |
| 7,713,305 B2* | 5/2010 | Ek | 623/20.14 |
| 8,012,217 B2 | 9/2011 | Strzepa et al. | |
| 2003/0135280 A1 | 7/2003 | Kopylov et al. | |
| 2003/0233149 A1 | 12/2003 | Hodorek | |
| 2004/0039447 A1* | 2/2004 | Simon et al. | 623/13.11 |
| 2004/0230303 A1* | 11/2004 | Gomes et al. | 623/16.11 |
| 2004/0230315 A1 | 11/2004 | Ek | |
| 2005/0033426 A1 | 2/2005 | Ogilvie et al. | |
| 2005/0084513 A1 | 4/2005 | Tang | |
| 2005/0137708 A1 | 6/2005 | Clark | |
| 2005/0137713 A1 | 6/2005 | Bertram | |
| 2006/0069446 A1 | 3/2006 | Ragusa et al. | |
| 2006/0190002 A1* | 8/2006 | Tallarida et al. | 606/102 |
| 2006/0229726 A1 | 10/2006 | Ek | |
| 2006/0241778 A1 | 10/2006 | Ogilvie | |
| 2007/0032876 A1 | 2/2007 | Clark | |
| 2007/0078334 A1 | 4/2007 | Scully et al. | |
| 2007/0123993 A1 | 5/2007 | Hassler et al. | |
| 2007/0198095 A1 | 8/2007 | VanDer Meulen et al. | |
| 2007/0225820 A1 | 9/2007 | Thomas et al. | |
| 2007/0250169 A1 | 10/2007 | Lang | |
| 2008/0188942 A1 | 8/2008 | Brown et al. | |
| 2009/0228104 A1 | 9/2009 | Strzepa et al. | |

FOREIGN PATENT DOCUMENTS

| | | |
|---|---|---|
| DE | 602004003510 T | 8/2007 |
| DE | 60126129 T | 11/2007 |
| EP | 1112753 A1 | 2/2001 |
| EP | 1437104 | 7/2004 |
| EP | 1955676 A1 | 8/2008 |
| ES | 2141533 T | 3/2000 |
| JP | 2004202233 A | 7/2004 |
| WO | WO-8802844 | 4/1988 |
| WO | WO-9012276 | 10/1990 |
| WO | WO-9203117 | 3/1992 |
| WO | WO-9409280 | 4/1994 |
| WO | WO-9602008 | 1/1996 |
| WO | WO-9710780 | 3/1997 |
| WO | WO-9819637 | 5/1998 |
| WO | WO-0013617 | 3/2000 |
| WO | WO-0133162 | 5/2001 |
| WO | WO-0170138 | 9/2001 |
| WO | WO-0243627 | 6/2002 |
| WO | WO-2004093767 | 11/2004 |
| WO | WO-2007041678 | 4/2007 |
| WO | WO-2007059459 | 5/2007 |
| WO | WO-2007103362 | 9/2007 |
| WO | WO-2007109752 | 9/2007 |
| WO | WO-2009111624 A2 | 9/2009 |
| WO | WO-2009111624 A3 | 12/2009 |

OTHER PUBLICATIONS

"Pyrocarbon in Orthopedics" downloaded from http://www.pyrocarbon.com/pyrocarbon-orthopedic-implant.php on Feb. 12, 2008, p. 1-4.

"Pyrolytic Carbon" downloaded from http://en.wikipedia.org/wiki/Pyrolytic_carbon on Feb. 12, 2008, p. 1-2.

PCT Internationa Search Report of the International Searching Authority for International Searching Authority for International Application No. PCT/US2009/049441, Aug. 26, 2009, p. 1-2.

PCT Written Opinion of the International Searching Authority for International Application No. PCT/US2009/049441, Aug. 26, 2009, p. 1-6.

PCT Internationa Search Report of the International Searching Authority for International Application No. PCT/US09/36159, May 13, 2009, p. 1-2.

PCT Written Opinion of the International Searching Authority for International Application No. PCT/US09/36159, May 13, 2009, p. 1-9.

"Pyrocarbon-Information for Surgeons" downloaded from http://www.pyrocarbon.com/index.php on Feb. 12, 2008.

Non-Final Office Action issued agains U.S. Appl. No. 12/074,770 on Oct. 28, 2009, p. 1-8.

Non-Final Office Action issued agains U.S. Appl. No. 12/074,770 on Dec. 28, 2009, p. 1-9.

Non-Final Office Action issued agains U.S. Appl. No. 12/074,770 on Apr. 27, 2010, p. 1-12.

Final Office Action issued against U.S. Appl. No. 12/074,770 on Aug. 31, 2010; p. 1-12.

PCT International Search Report Issued in Connection with International Application No. PCT/US2010/046654; Nov. 29, 2010; 1-5 pages.

PCT Written Opinion of the International Searching Authority Issued in Connection with International Application No. PCT/US2010/046654; Nov. 29, 2010; 1-8 pages.

Non-Final Office Action Issued Against U.S. Appl. No. 12/074,770; Nov. 24, 2010; 1-14 pages.

Non-Final Office Action Issued Against U.S. Appl. No. 12/319,869; Nov. 29, 2010; 1-16 pages.

U.S. Patent and Trademark Office; Notice of Allowance and Fee(s) Due Issued in Connection with U.S. Appl. No. 12/319,869; Jun. 24, 2011; 13 pages; U.S.A.

U.S. Patent and Trademark Office; Non-Final Office Action Issued Against U.S. Appl. No. 12/396,872; Jul. 6, 2011; 18 pages; U.S.A.

* cited by examiner

METHOD OF USE OF TROCHLEAR IMPLANTS

CROSS-REFERENCE TO RELATED APPLICATIONS

This application is a divisional patent application of U.S. patent application Ser. No. 12/868,112, filed on Aug. 25, 2010, which claims the benefit and priority of U.S. Provisional Patent Application Ser. No. 61/236,811 filed Aug. 25, 2009.

FIELD OF THE INVENTION

This disclosure relates to methods of use of trochlear implants for the repair of articular cartilage defects. Particular embodiments of this disclosure relate to methods of use of implants that serve as a replacement for diseased or damaged cartilage in joints such as human knees, including the trochlear groove, hips and shoulders.

BACKGROUND OF THE INVENTION

Cartilage acts as a pad between bones to reduce friction and prevent the bones from grinding against one another. Cartilage covers the articular surface of many, if not all, joints in the body. The smoothness and thickness of the cartilage are factors that determine the load-bearing characteristics and mobility of the joints. Over time, due to injury or heredity, however, lesions such as fissures, cracks or crazes can form in the cartilage. In some cases, osteochondral, the lesion penetrates to the subchondral surface of the bone. In other cases, chondral, the lesion does not penetrate to the subchondral surface of the bone. Lesions generally do not repair themselves—and if any repair is made it is generally insufficient to heal—leading to significant pain and disability, either acutely or over time.

One approach for regenerating new cartilage is autologous chondrocyte transplantation. This technique is complex and relatively costly. Other techniques, aimed at repair instead of regeneration, include debridement, lavage, microfracturing, drilling, and abrasion arthroplasty. These procedures generally involve penetrating the region of vascularization in the subchondral bone with an instrument until bleeding occurs. Formation of a fibrin clot differentiates into fibrocartilage, which then covers the defect site.

An alternative approach has been to undergo a total replacement of the joint. Such total replacements, however, are costly, high risk, and involve a long recovery time.

SUMMARY OF THE INVENTION

Definitions

In various illustrative embodiments, the terms "vertical axis" or "vertical" mean a direction from the top of a three-dimensional object to the bottom of the three-dimensional object.

In various illustrative embodiments, the terms "horizontal axis" or "horizontal" mean a direction from right of the three-dimensional object to the left of the three-dimensional object.

In various illustrative embodiments, the terms "depth axis" or "depth" mean a direction from the front of the three-dimensional object to the back of the three-dimensional object.

In various illustrative embodiments, the term "medial side" is made with reference to the medial side of a patient's joint.

In various illustrative embodiments, the term "lateral side" is made with reference to the lateral side of a patient's joint.

In various illustrative embodiments, the term "torus" means the surface of a toroid.

In various illustrative embodiments, the term "tubular radius" refers to the radius of the tube of a torus, as opposed to the "major radius" or "radius of revolution", which are terms that refer to the radius from the center of the torus to the center of the tube.

In various illustrative embodiments, geometric terms such as "elliptical," "oval", "circle", "sphere", "cylinder", and the like are used as references and for clarity of understanding, as would be understood by one of ordinary skill in the art. Accordingly, these terms should not be limited to strict Euclidean standard.

In accordance with an aspect of an illustrating embodiment of the present invention, a method of repairing articular cartilage using the implant device is provided. The method of this illustrative embodiment may include locating articular cartilage having a lesion. An implant device, as described above, may be selected preferably having dimensions compatible with the lesion. A hole may be formed through the cartilage and subchondral bone, into the cancellous bone. The implant device may be inserted into the hole so that the lower and side surfaces of the articular end of the implant device abut against the prepared subchondral and cancellous bone and the stem of the implant device abuts against the prepared cancellous bone.

In the detailed description which follows in conjunction with the drawings, like parts are given like reference numerals, and the vertical, horizontal and depth axes of a given embodiment are specified explicitly in at least one drawing of an illustrative embodiment.

BRIEF DESCRIPTION OF THE DRAWINGS

The drawing figures are not necessarily to scale and certain features may be shown exaggerated in scale or in somewhat schematic form in the interest of clarity and conciseness, wherein.

DISCLOSURE OF ALTERNATIVE EMBODIMENTS

Figure 1:
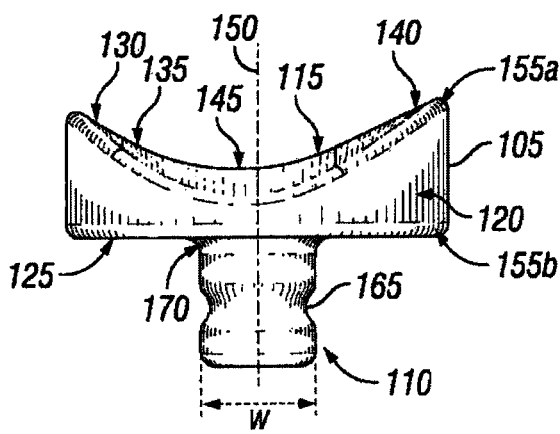
FIG. 1 is a side view of one embodiment of an implant.
Figure 2:
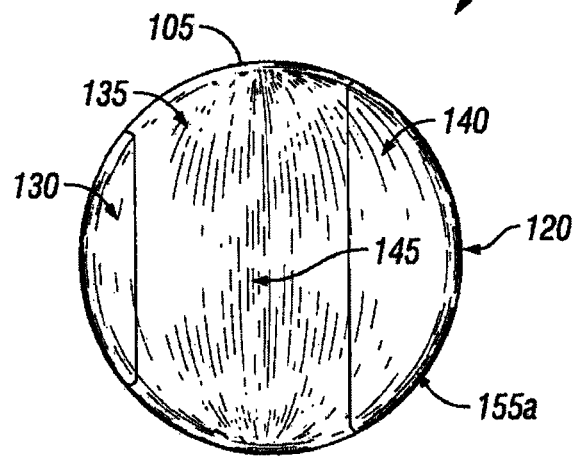
FIG. 2 is a top-down view of the implant of FIG. 1.
Figure 3:
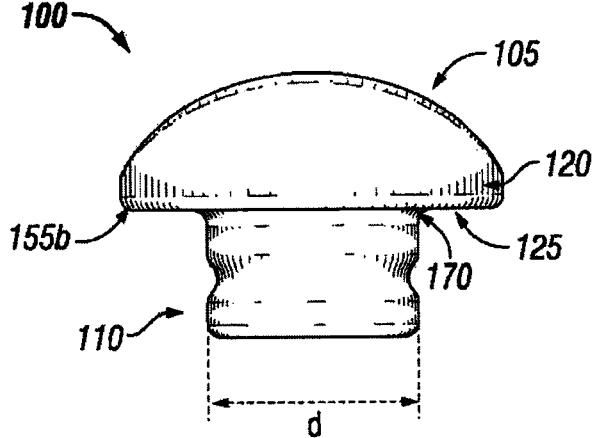
FIG. 3 is an alternative side view of the implant of FIG. 1.
Figure 4:
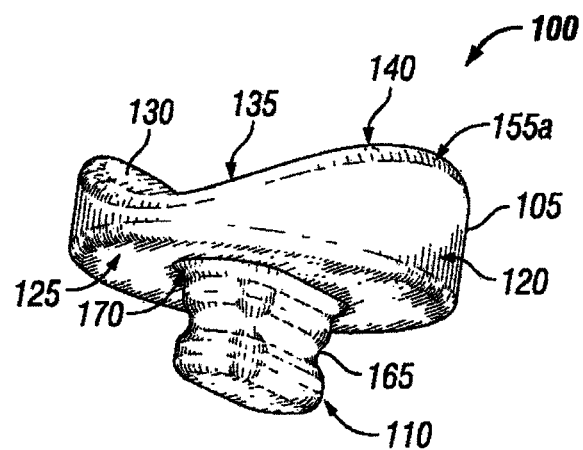
FIG. 4 is a perspective view of the implant of FIG. 1.
Figure 5:
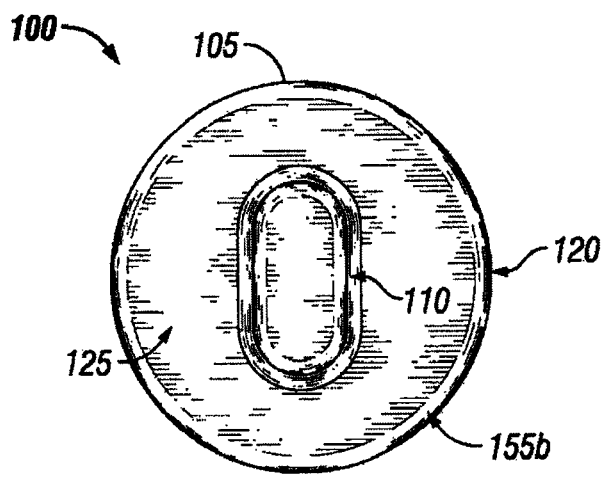
FIG. 5 is a bottom-up view of the implant of FIG. 1.
Figure 6:
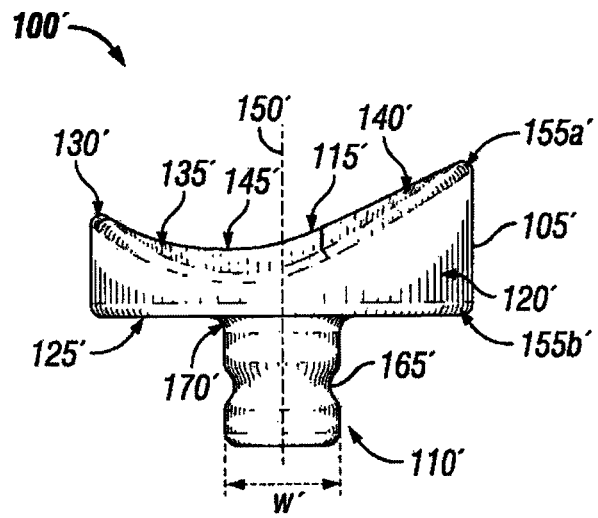
FIG. 6 side view of an alternative embodiment of an implant.

FIGS. 1 and 6 are illustrative embodiments of an implant 100, 100' in which the vertical, V, horizontal, H, and depth, D, axes of this embodiment are depicted. The implant 100, 100' may have an articular end 105, 105' and a stem 110, 110'. The articular end 105, 105' may be bound by three surfaces: an upper surface 115, 115' a side surface 120, 120' and a lower surface 125, 125'. The upper surface 115, 115' and the lower surface 125, 125' may each intersect the side surface 120, 120'. In an embodiment, the upper surface 115, 115' may have a surface normal (not shown) at the saddle point 145, 145' (described below) that may be approximately perpendicular to the lower surface 125, 125'. In an embodiment, a tangent H-D plane (not shown) to the saddle point 145, 145' (descried below) may be approximately parallel to the lower surface

125, 125'. All of the surfaces of the articular end 105, 105' preferably blend 155a, 155a' into one another. The blend 155a, 155a' may have an edge radius ranging from between about 0.1 millimeters to about 2 millimeters, alternatively about 1 millimeter, alternatively about 0.75 millimeters, and alternatively about 0.5 millimeters.

The upper surface 115, 115' may be generally saddle shaped. For ease of reference, the upper surface 115, 115' may be thought of as segmented into three regions of surface curvature: a first surface curvature 130, 130', a central surface curvature 135, 135', and a second surface curvature 140, 140'. The central surface curvature 135, 135' may be tangent to, on its medial side, the first surface curvature 130, 130'. The central surface curvature 135, 135' may be tangent to, on its lateral side, the second surface curvature 140, 140'.

The first surface curvature 130, 130' may be formed of, or along, a partial right circular cone having an aperture ranging from between about 20° to about 80°, alternatively from between about 30° to about 70°, alternatively from between about 40° to about 60°, alternatively about 40°, alternatively about 50°, alternatively about 60°. The central surface curvature 135, 135' may be formed of, or along, a partial torus having a minor radius ranging from between about 8 millimeters to about 40 millimeters, alternatively from between about 8 millimeters to about 30 millimeters, alternatively about 10 millimeters, alternatively about 12 millimeters, alternatively about 15 millimeters, and having a major radius ranging from between about 25 millimeters to about 70 millimeters, alternatively from between about 28 millimeters to about 68 millimeters, alternatively about 45 millimeters, alternatively about 48 millimeters, alternatively about 50 millimeters. The second surface curvature 140, 140' may be formed of, or along, a partial right circular cone having an aperture ranging from between about 20° to about 80°, alternatively from between about 30° to about 70°, alternatively from between about 30° to about 50°, alternatively about 30°, alternatively about 40°, alternatively about 50°. In an embodiment, the aperture of the first surface curvature 130, 130' may be between about 5° to about 15°, alternatively about 10°, greater than the aperture of the second surface curvature 140, 140'.

Figure 7:
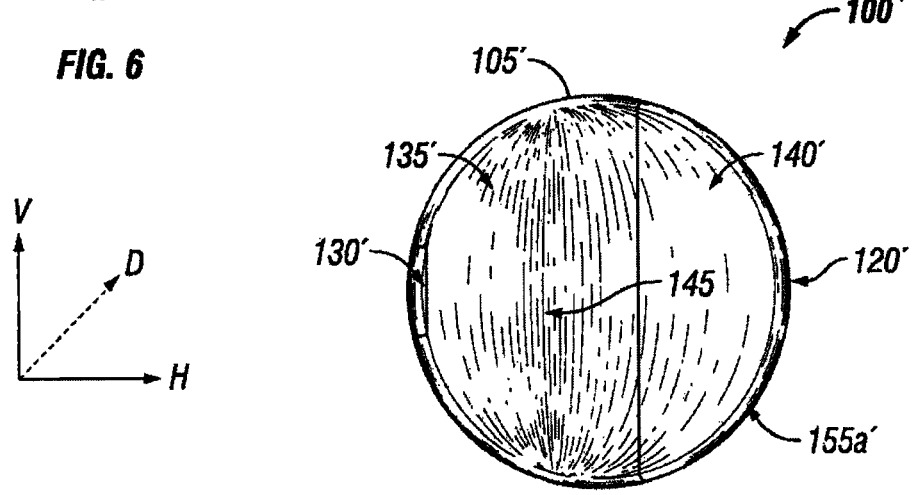
FIG. 7 is a top-down view of the implant of FIG. 6.
Figure 8:
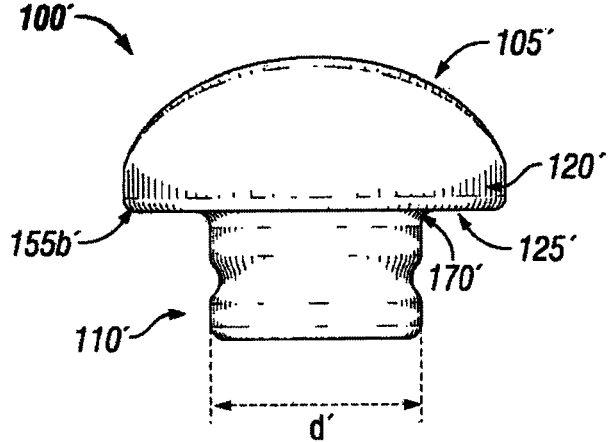
FIG. 8 is an alternative side view of the implant of FIG. 6.

In an embodiment, the major radius of the central surface curvature 135, 135' may be in a plane that may be offset in any direction from a central axis 150, 150' of the stem 110, 110' by an amount ranging from between about 0 to about 5 millimeters, alternatively from between about 1 to about 4 millimeters, alternatively about 3 millimeters, alternatively about 1 millimeter. In an embodiment, the major radius of the central surface curvature 135, 135' may be in a plane that may be offset, along the H axis towards either the medial or lateral side of the implant 100, 100', from a central axis 150, 150' of the stem 110, 110' by an amount ranging from between about 0 to about 5 millimeters, alternatively from between about 1 to about 4 millimeters, alternatively about 3 millimeters, alternatively about 1 millimeter. FIGS. 1-5 illustrate an implant 100 having a one millimeter medial offset and FIGS. 6-8 illustrate an implant 100' having a three millimeter medial offset. The central surface curvature 135, 135' may include, at its central position along its surface, a saddle point 145, 145'. In an embodiment, the length, along the vertical axis, from the saddle point 145, 145' on the surface of the central surface curvature 135, 135', to the lower surface 125, 125' may range from between about 1 millimeter to about 6 millimeters, alternatively from between about 1 millimeter to about 5 millimeters, alternatively about 3.5 millimeters, and alternatively about 4.5 millimeters.

With reference to FIGS. 2, 4, 5, and 7, the side surface 120, 120' of the articular end 105, 105' may be generally cylindrical, and may have a diameter ranging from between about 10 millimeters to about 40 millimeters, alternatively from about 10 millimeters to about 30 millimeters, alternatively from about 20 millimeters to about 30 millimeters, alternatively about 25 millimeters, alternatively about 20 millimeters.

With reference to FIGS. 1, 3-6, and 8, the lower surface 125, 125' may be generally planar, and together with the side surface 120, 120' may form a generally right circular cylinder. The lower surface 125, 125' may further blend into the side surface 120, 120'. The further blend 155b, 155b' may have an edge radius ranging from between about 0.1 millimeters to about 2 millimeters, alternatively about 1 millimeter, alternatively about 0.75 millimeters, and alternatively about 0.5 millimeters.

The stem 110, 110' may extend from the lower surface 125, 125' of the articular end 105, 105' in a general direction, along the vertical, V, axis away from the central surface curvature 135, 135', a length ranging from between about 2 millimeters to about 10 millimeters, alternatively from about 4 millimeters to about 7 millimeters, alternatively about 5.5 millimeters. In an embodiment, the articular end 105, 105' and the stem 110, 110' are formed as a non-modular, uni-body, i.e., one integral piece without intervening mechanical connection.

The stem 110, 110' may be formed of a single cylinder, a single-truncated conical shape, a protrusion having an oval-shaped cross-section, or an elliptic cylindrical shape. In an embodiment, the stem 110, 110' may have a width, w, along the horizontal, H, axis of the stem 110, 110' that may range from between about 1 millimeter to about 10 millimeters, alternatively from between about 3 millimeters to about 7 millimeters, alternatively about 5 millimeters, alternatively about 6 millimeters. In an embodiment, the stem 110, 110', may have a depth, d, along the depth, D, axis of the stem 110, 110' that may range from between about 5 millimeters to about 40 millimeters, alternatively from between about 8 millimeter to about 20 millimeters, alternatively about 10 millimeters, alternatively about 11.5 millimeters, alternatively about 13 millimeters. The lower surface 125, 125' of the articular end 105, 105' may blend into the stem 110, 110' with a corner fillet 170, 170'. The corner fillet 170, 170' may have a radius of about 1.5 millimeters.

The stem 110, 110' may include one, or more, grooves 165, 165' about its perimeter. The shape of the groove(s) 165, 165' may be defined by a partial oval-shaped torus having a tubular radius ranging from about 0.25 millimeters to about 2 millimeters, alternatively from about 0.5 millimeters to about 1.75 millimeters, alternatively about 1.75 millimeters, alternatively about 1 millimeter. The groove(s) 165, 165' may blend into the stem 110, 110' with a blend having an edge radius of from about 0.1 millimeters to about 1 millimeters, alternatively about 0.8 millimeters.

The implant 100, 100' many be manufactured from a variety of suitable materials, having the requisite strength and biocompatibility characteristics to function as an implant, including but not limited to any of the following, individually or in combination, graphite, pyrocarbon, ceramic, aluminum oxide, silicone nitride, silicone carbide or zirconium oxide; metal and metal alloys, e.g., Co—Cr—W—Ni, Co—Cr—Mo, CoCr alloys, CoCr molybdenum alloys, Cr—Ni—Mn alloys; powder metal alloys, 316L or other stainless steels, Ti and Ti alloys including Ti 6A1-ELI; polymers, e.g., polyurethane, polyethylene, polypropylene, thermoplastic elastomers, polyaryletherketones such as polyetherehterketone (PEEK) or polyetherketoneketone (PEKK); biomaterials such as polycaprolactone; and diffusion hardened materials such as Ti13-13, zirconium and niobium. Moreover, the implant 100, 100' may be coated with a variety of suitable materials, including any of the following, individually or in combination, porous coating systems on bone-contacting surfaces, hydrophilic coatings on load-bearing surfaces, hydroxyapatite coatings on bone-contacting surfaces, and tricalcium phosphate on bone-contacting surfaces. Other suitable coatings include growth factors and other biological agents such as bone morphogenetic proteins (BMP's), transforming growth factor beta, among others. In an embodiment, the outer coating of the implant 100, 100' may be harder than the core of the implant 100, 100'. Additionally, components of the invention may be molded or cast, hand-fabricated or machined.

In an illustrative embodiment, the implant 100, 100' is composed of graphite and pyrocarbon. Preferably, the implant 100, 100' is graphite and includes a coating of pyrocarbon. The pyrocarbon coating may have an average thickness of from about 100 to about 1000 microns, alternatively from about 200 microns to about 500 microns, alternatively from about 250 to about 500 microns, alternatively about 350 microns. The pyrocarbon coating may have an elastic modulus from about 15 gigapascals ("GPa") to about 22 GPa, alternatively about 20 GPa. The pyrocarbon coating may further have a strength of at least 200 megapascals ("MPa"), alternatively at least about 300 MPa, alternatively at least about 400 MPa. The pyrocarbon elastic modulus and strength are preferably tested using four-point bend, third-point-loading substrated specimens of dimensions 25 millimeters by 6 millimeters by 0.4 millimeters. Preferably the pyrocarbon is pyrolytic carbon as described in *Pure Pyrolytic Carbon: Preparation and Properties of a New Material, On-X Carbon for Mechanical Heart Valve Prostheses*, Ely et al, J. Heart Valve Dis., Vol. 7, No. 6, A00534 (November 1998), alternatively pyrocarbon is pyrolytic carbon as described in the before-mentioned J. Heart Valve Dis. publication, but includes additional silicon.

The above-described implants 100, 100' may be used to repair damaged articular cartilage in humans, including ankles, knees, wrists, elbows, shoulders, and the like joints. In another illustrative embodiment or a preferred method, a patient having articular cartilage damage may be identified. The patient is preferably fully informed of the risks associated of surgery, and consents to the same. An incision may be made near the damaged articular cartilage. The lesion to be repaired may be identified, and a implant having dimensions compatible with the lesion may be selected. The implant may be slightly smaller or slightly larger than the lesion. In these embodiments, the implant may be from about 0.1 percent to about 20 percent smaller or larger than the lesion. A hole is then formed, i.e., drilled, punched, or broached, through the cartilage and the subchondral bone into the cancellous bone. Preferably, the dimensions of the hole are slightly less than the horizontal and depth dimensions of the stem 110, 110' and the articular end 105, 105' of the implant 100, 100'. This may be achieved, for example, by using a box chisel and then a dill bit. Preferably the minimum length of the hole is equal to or slightly greater than the length of the stem 110, 110' of the implant 100, 100', along the central axis 150, 150' of the stem 110, 100' plus the length from the lower surface 125, 125', to the saddle point 145, 145'. An amount of healthy and damaged cartilage may be removed near the lesion so that the lower surface 125, 125' of the articular end 105, 105' may rest against the patient's bone. The stem 110, 110' of the implant 100, 100' may be inserted into the hole, and the lower surface 125, 125' of the implant's 100, 100' articular end 105, 105' may rest against the bone. The incision is then sutured by any of several known methods.

While specific alternatives to steps of the specific embodiments have been described herein, additional alternatives not specifically disclosed but known in the art are intended to fall within the scope of the invention. For example, while specific dimensions, and ranges of dimensions, have been provided further dimensions may reasonably fall within the scope of the invention. Thus, it is understood that other applications of the present invention will be apparent to those skilled in the art upon reading the descriptions of the described illustrative embodiments and after consideration of the appended claims and drawings.

The invention claimed is:

1. A method of repairing articular cartilage comprising:
   (a) locating articular cartilage having a lesion;
   (b) utilizing an implant having dimensions compatible with the lesion, wherein the implant comprises;
      (i) an articular end having an upper surface, a side surface, and a lower surface;
         wherein the upper surface and lower surface each intersect the side surface, the upper surface has a first surface curvature, a central surface curvature, and a second surface curvature; and
         wherein the upper surface blends into the side surface, the side surface blends into the upper surface and the lower surface, and the lower surface blends into the side surface, and wherein each blend has an edge radius of from about 0.1 millimeters to about 2 millimeters; and
      (ii) an oval-shaped stem, which extends from the lower surface in a direction away from the upper surface of the articular end;
   (c) forming a cavity in the articular cartilage, subchondral bone, and cancellous bone; and
   (d) engaging the implant with the cavity so that the lower and side surfaces of the articular end abut against the subchondral and cancellous bone and the stem abuts against the cancellous bone.

2. The method of claim 1, wherein the first surface curvature is formed along a partial right circular cone having an aperture ranging from between about 20° to about 80°, the central surface curvature is formed along a partial torus having a minor radius ranging from between about 8 millimeters to about 40 millimeters and a major radius ranging from about 25 millimeters to about 70 millimeters, and the second surface curvature is formed along a partial right circular cone having an aperture ranging from between about 20° to about 80°, and the oval-shaped stem has at least one groove about its perimeter, the at least one groove defined by a partial oval-shaped torus having a tubular radius ranging from about 0.25 millimeters to about 2 millimeters.

3. The method of claim 1, wherein forming the cavity includes placement of autograft, allograft bone, or various bone graft substitute material into the lesion.

4. The method of claim 1, wherein the first surface curvature is formed along a partial right circular cone having an aperture ranging from between about 20° to about 80°, the central surface curvature is formed along a partial torus having a minor radius ranging from between about 8 millimeters to about 40 millimeters and a major radius ranging from about 25 millimeters to about 70 millimeters, and the second surface curvature is formed along a partial right circular cone having an aperture ranging from between about 20° to about 80°.

5. The method of claim 4, wherein the first surface curvature is formed along a partial right circular cone having an aperture ranging from between about 40° to about 60°, the central surface curvature is formed along a partial torus having a minor radius of about 12 millimeters and a major radius of about 48 millimeters, and the second surface curvature is formed along a partial right circular cone having an aperture ranging from between about 30° to about 50°, wherein the first surface aperture is between about 5° to about 15° greater than the second surface aperture.

6. The method of claim 5, wherein the central surface curvature has a saddle point and the stem has a central axis, and wherein the location of the saddle point is offset, along a horizontal direction towards a medial side of the implant, from the location of the central axis by a distance ranging from between about 1 to about 5 millimeters.

7. The method of claim 6, wherein a length, along a vertical axis parallel to the central axis of the stem, from the saddle point to a lower surface of the articular head ranges from between about 1 millimeter to about 6 millimeters.

8. The method of claim 7, wherein the side surface of the articular end is generally cylindrical, and has a diameter ranging from between about 10 millimeters to about 40 millimeters.

9. The method of claim 8, wherein the diameter is about 20 millimeters, the offset is either 1 millimeter or 3 millimeters, the first surface curvature is formed along a partial cone having an aperture selected from the group consisting of 40°, 50°, and 60°, and the second surface curvature is formed along a partial cone having an aperture angle selected from the group consisting of 30°, 40°, and 50°, and wherein the first surface aperture is 10° greater than the second surface aperture.

10. The method of claim 8, wherein the diameter is about 25 millimeters, the offset is either 1 millimeter or 3 millimeters, the first surface curvature is formed along a partial cone having an aperture selected from the group consisting of 40° and 50°, and the second surface curvature is formed along a partial cone having an aperture selected from the group consisting of 30° and 40°, and wherein the first surface aperture is 10° greater than the second surface aperture.

11. The method of claim 1, wherein the oval-shaped stem has a width distance ranging from between about 1 millimeter to about 6 millimeters and a depth distance ranging from between about 5 millimeters and about 40 millimeters.

12. The method of claim 11, wherein the oval-shaped stem has at least one groove about its perimeter, the at least one groove defined by a partial oval-shaped torus having a tubular radius ranging from about 0.25 millimeters to about 2 millimeters.

13. The method of claim 1, wherein each blend has an edge radius of about 0.8 millimeters.

14. The method of claim 11, wherein the lower surface of the articular end blends into the oval-shaped stem with a corner fillet, the corner fillet having a radius of about 1.5 millimeters.

15. The method of claim 1, wherein the articular end and the oval-shaped stem are formed from graphite and pyrocarbon.

16. The method of claim 15, wherein the articular end and the oval-shaped stem comprise a graphite core and a pyrocarbon coating, the pyrocarbon coating having an elastic modulus from about 15 GPa to about 22 GPa, the pyrocarbon coating having an average thickness ranging from about 100 to about 1000 microns.

17. The method of claim 16, wherein the pyrocarbon coating has an elastic modulus of about 20 GPa and a strength of at least 400 MPa.

18. The method of claim 17, wherein the upper surface and contiguous edge blends are polished, and the lower surface and stem are coated with hydroxyapatite.

19. The method of claim 18, wherein the pyrocarbon coating is harder than the graphite core.

20. The method of claim 1, wherein the oval-shaped stem having at least one groove about a perimeter of the oval-shaped stem, the groove defined by a partial oval-shaped torus having a groove tubular radius ranging from about 0.25 millimeters to about 2 millimeters, the groove blending into the stem with a groove blend having an edge radius ranging from about 0.1 millimeters to about 1 millimeter.

* * * * *